United States Patent [19]

Menasche

[11] Patent Number: 4,927,412
[45] Date of Patent: May 22, 1990

[54] CORONARY SINUS CATHETER

[75] Inventor: Philippe Menasche, Paris, France

[73] Assignee: Retroperfusion Systems, Inc., Costa Mesa, Calif.

[21] Appl. No.: 282,004

[22] Filed: Dec. 8, 1988

[51] Int. Cl.⁵ .............................................. A61M 25/00
[52] U.S. Cl. ...................................... 604/96; 606/192
[58] Field of Search ................................. 604/96–103; 128/344; 606/192

[56] References Cited

U.S. PATENT DOCUMENTS 4,689,041 8/1987 Corday et al. ...................... 604/99
4,721,109 1/1988 Healey ................................ 604/96

Primary Examiner—Stephen C. Pellegrino
Attorney, Agent, or Firm—Flehr, Hohbach, Test, Albritton & Herbert

[57] ABSTRACT

A coronary sinus catheter having a flexible elongate member with proximal and distal extremities. The flexible elongate member has at least two lumens extending longitudinally thereof. A balloon is mounted on the distal extremity of the flexible elongate member and has its interior in communication with one of the lumens. The balloon has at least one truncated conical surface with outwardly facing spaced apart parallel concentric lands formed thereon for frictionally engaging the coronary sinus to provide a high retentive force for the catheter.

8 Claims, 1 Drawing Sheet

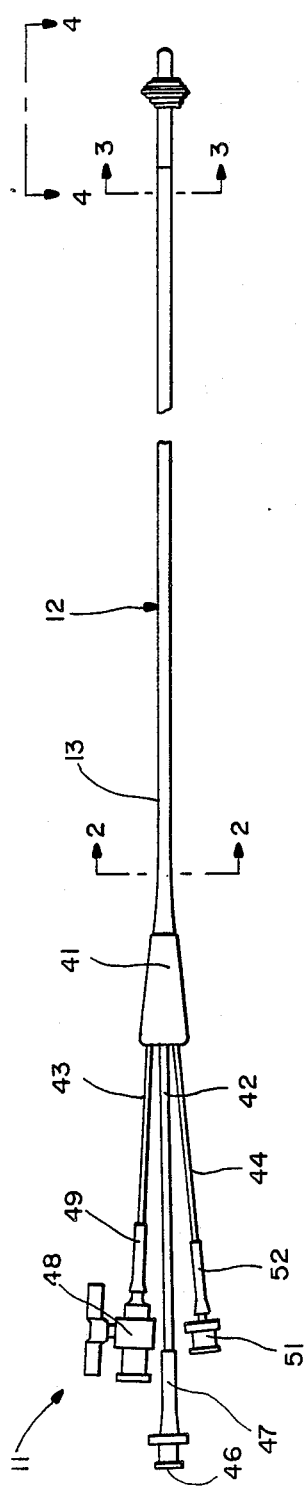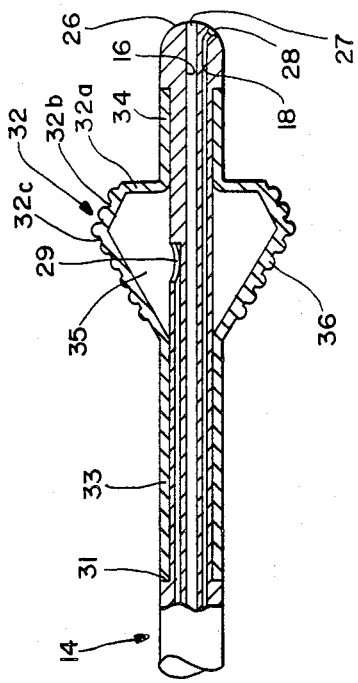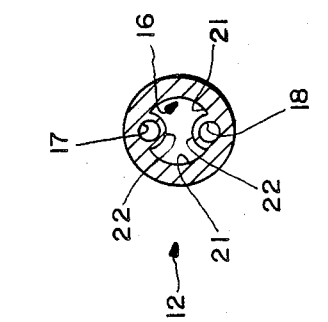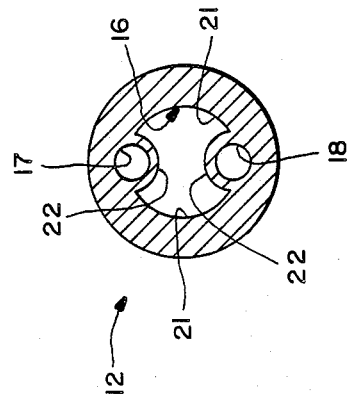

CORONARY SINUS CATHETER

This invention relates to a coronary sinus catheter and more particular to a coronary sinus catheter for use in surgical procedures utilizing cardioplegia.

Retrograde coronary sinus perfusion cannulae have heretofore been provided. In an article entitled "Retrograde cardioplegia: myccardial protection via the coronary veins—1986" by S.R. Gundry published in Annals of Thoracic Surgery, Kirsa, Vol. 38, No. 2, Aug. 1984, pages 73–80, there is an extensive background discussion of the various techniques which have heretofore been utilized for delivering cardioplegia solutions in a retrograde fashion into the heart. It has been found that with cannulae which have been provided with balloons that the distal extremities have a tendency to be ejected from the coronary sinus because the sinus walls are slippery, extensible and are tapered so that the sinus vessels become smaller in the direction in which the cannula is advanced into the sinus vessel. There is therefore a need for a new and improved device which can be utilized during cardioplegia It is an object of the present invention to provide a coronary sinus catheter which has enhanced capabilities for retention and stability within the coronary sinus.

Another object of the invention is to provide a catheter of the above character which can be utilized for making pressure measurements.

Additional objects and features of the invention will appear from the following description in which the preferred embodiments are set forth in detail in conjunction with the accompanying drawings.

FIG. 1 is a plan view of a coronary sinus catheter incorporating the present invention.

FIG. 2 is an enlarged cross-sectional view taken along the line 2—2 of FIG. 1.

FIG. 3 is an enlarged cross-sectional view taken along the line 3—3 of FIG. 1.

FIG. 4 is an enlarged view partially in cross section of the distal extremity of the catheter shown in FIG. 1.

In general, the coronary sinus catheter is comprised of a flexible elongate member having at least two lumens extending longitudinally thereof. The member is provided with proximal and distal extremities. An inflatable balloon is mounted on the distal extremity of the flexible elongate member and has its interior in communication with one of &:he lumens. The balloon is provided with at least one conical surface facing toward the distal extremity of the catheter. This conical surface is provided with externally facing substantially concentric and spaced apart parallel lands or ridges which are adapted to engage the coronary sinus to provide a high retentive force for the catheter in the coronary sinus.

More in particular as shown in the drawings, the coronary sinus catheter assembly 11 consists of a flexible elongate member 12 which can be formed in a suitable manner such as by extruding thermoplastic polyurethane having a suitable hardness as, for example, 55 Shore D. The member 12 can have a usable length as, for example, 20 to 100 centimeters and preferably a usable length of approximately 30 centimeters.

As shown in FIGS. 2 and 3, the flexible elongate member has a cylindrical outer surface which at its proximal extremity 13 can have a suitable outside diameter as, for example, 0.230 inches and at the distal extremity 14 an outside diameter of approximately 0.140 inches. The flexible elongate member 12 is provided with at least two lumens and preferably 3 lumens 16, 17 and 18 as shown in FIGS. 2 and 3 with the lumen 16 serving as an infusion lumen, the lumen 17 serving as a balloon inflation lumen and lumen 18 serving as a pressure lumen. The balloon inflation lumen 17 and the pressure Iumen 18 generally are circular in cross section and can be of the same size. For example, they can have an inside diameter of 0.041 inches at the proximal extremity and approximately, 0.025 inches at the distal extremity. In order to provide an infusion lumen 16 as large as possible that can be accommodated within the flexible elongate member 12, as well as to maintain adequate column strength, the lumen 16 has a particular shape with diametrically opposed side walls 21 being part of a cylindrical surface having a suitable diameter such as 0.131 inches at the proximal extremity and 0.080 inches at the distal extremity. The opposite side walls 22 form the other portions of the side wall for the lumen 16 and are defined by concave recesses which are a part of a surface of a cylinder having a radius of approximately 0.036 inches at the proximal extremity and 0.022 inches at the distal extremity.

The extreme distal extremity of the flexible elongate member 12 is provided with a rounded tip 26 which is generally hemispherical in shape. The infusion lumen 16 extends through the tip 26 and opens through an infusion port 27. The pressure lumen 18 also extends through the tip 26 and opens through a pressure port 28. The balloon inflation lumen terminates short of the tip 26 and opens through a balloon inflation and deflation port 29.

An annular recess 31 is formed in the distal extremity 14 of the flexible elongate member 12 and has a suitable length as, for example, approximately 1.24 inches. The recess is spaced at a suitable distance, as for example, 0.190 inches from the distal extremity of the tip 26. An inflatable balloon 32 having proximal and distal extremities 33 and 34 is secured within the annular recess 31 by suitable means such as by a primer and a silicone adhesive of conventional types. It can be seen that the overall thicknesses of the proximal and distal extremities 33 and 34 corresponds to the depth of the annular recess 31 so that the outer surfaces of the proximal and distal extremities 33 and 34 are flush with the outer surface of the flexible elongate member 12.

The balloon 32 is provided with an interior space 35 which is in communication with the balloon inflation and deflation port 29. The balloon 32 is formed of a suitable elastomeric material such as a silicone rubber having a suitable hardress, as for example, 50 Shore A. As shown in FIG. 4, the balloon 32 has been molded to a particular configuration. The balloon 32 is provided with a radially extending portion 32a that extends in a direction perpendicular to the longitudinal axis of the flexible elongate member 12. The portion 32a adjoins the cylindrical distal extremity 34 of the balloon. The balloon is also provided with truncated conical portions 32b and 32c in which the portion 32b adjoins the portion 32a and extends at an angle thereto of approximately 115° and another portion 32c which adjoins the portion 32b and extends at a suitable angle thereto as, for example, approximately 210°. The exterior surfaces of the truncated conical portions 32b and 32c of the balloon 32 are provided with spaced apart parallel concentric outwardly facing lands 36. As can be seen the lands 36 in cross section are generally hemispherical in shape and have a radius of approximately 0.015 inches and are spaced apart a distance of approximately 0.05 inches.

The balloon has a wall thickness of approximately 0.030 inches. As shown in FIG. 4 the imaginary apex of the truncated conical portion 32c faces away from the distal extremity of the catheter 11 whereas the imaginary apex of the conical portion 32b faces towards the distal extremity of the catheter 11.

A molded fitting 41 formed of a suitable material such as Pebax is provided on the proximal extremity 13 and receives flexible tubular members 42, 43 and 44 with tubular member 42 being in communication with the infusion lumen 16, with the tubular member 43 being in communication with the balloon inflation lumen 17 and with the tubular member 44 being in communication with the pressure lumen 18. In order to aid the physician utilizing the device, the members 42, 43 and 44 can be color coded. For example, the tubular member 42 can be transparent, the tubular member 43 can be red and the tubular member 44 can be blue. A fitting 46 is mounted in the proximal extremity of the tubular member 42 and is retained therein by a suitable adhesive such as a cyanoacrylate and by a shrink wrap 47. The tubular member 43 for the balloon inflation lumen is provided with a one-way stopcock 48 of a suitable type such as one manufactured by Baxer Pharmaseal, a division of Baxter International of Deerfield, Illinois. It is also held in place by a suitable adhesive such as a cyanoacrylate and by a shrink wrap 49. A Luer-type fitting 51 is mounted on the proximal extremity of the tubular member 44 and is also retained thereon by a suitable adhesive such as a cyanoacrylate and by a shrink wrap 52.

Operation and use of the coronary sinus catheter for utilization during cardioplegia may now be briefly described as follows. The cardioplegia catheter is intended to be placed in the coronary sinus of the patient during open heart surgery and is intended to provide nutrient solutions to the myocardium to support the heart muscle during the time that the operation is taking place when the heart is not beating, that is, during cardioplegia. The catheter is utilized in a conventional manner by making an incision in the heart and advancing the catheter into the coronary sinus. When the catheter is in the desired position, the balloon 32 is inflated. It has been found that the particular shape of the balloon with the lands thereon adapts the balloon for engaging the tissue forming the sinus so that the balloon is retained within the sinus with a high retentive force which cannot be readily dislodged and therefore serves to maintain the catheter in the desired position. Additionally, this shape reduces the possibility of occluding other vessels which intersect the coronary sinus near its entrance. After the catheter has been positioned, nutrient solutions can be introduced through the infusion lumen in a manner well known to those skilled in the art. Similarly, pressure measurements can be made by measuring the pressure at the pressure port 28 in a conventional manner.

After the operation has been completed, the coronary sinus catheter can be readily removed after deflating the balloon.

What is claimed is:

1. In a coronary sinus catheter, a flexible elongate member having proximal and distal extremities, the flexible elongate member having at least two lumens extending longitudinally thereof, a balloon mounted on the distal extremity of the flexible elongate member and having its interior in communication with one of the lumens, the balloon having at least one truncated conical surface having outwardly facing spaced apart parallel concentric lands formed thereon for frictionally engaging the coronary sinus to provide a high retentive force for the catheter.

2. A catheter as in claim 1 in which the truncated conical portion has an imaginary apex which faces away from the distal extremity of the flexible elongate member.

3. A catheter as in claim 1 in which the truncated conical portion has an imaginary apex which faces towards the distal extremity of the flexible elongate member.

4. A catheter as in claim 1 wherein the balloon is provided with a radially extending portion which adjoins the first named conical surface.

5. A catheter as in claim 1 wherein said balloon is formed of a silicone rubber.

6. A catheter as in claim 1 wherein said balloon has a wall thickness of approximately 0.03 inches and wherein said lands are generally hemispherical in cross section and have a radius of approximately 0.015 inches.

7. A catheter as in claim 7 wherein said lands are spaced apart approximately 0.050 inches.

8. In a coronary sinus catheter, a flexible elongate member having proximal and distal extremities, the flexible elongate member having at least two lumens extending longitudinally thereof, a balloon mounted on the distal extremity of the flexible elongate member and having its interior in communication with one of the lumens, the balloon having at least one truncated conical surface having outwardly facing spaced apart parallel concentric lands formed thereon for frictionally engaging the coronary sinus to provide a high retentive force for the catheter, said balloon being provided with a second truncated conical surface adjoining the first named conical surface and having outwardly facing spaced apart parallel concentric lands formed thereon.

* * * * *